United States Patent
Ueda et al.

(10) Patent No.: US 11,262,345 B2
(45) Date of Patent: Mar. 1, 2022

(54) METHOD FOR MEASURING GLYCATED PROTEIN USING INTERDIGITATED ELECTRODE

(71) Applicant: Ultizyme International Ltd., Tokyo (JP)

(72) Inventors: Yuki Ueda, Tokyo (JP); Koji Sode, Tokyo (JP); Wakako Tsugawa, Tokyo (JP); Masaaki Kurita, Kanagawa (JP); Takashi Nishimori, Kanagawa (JP)

(73) Assignee: Ultizyme International Ltd., Tokyo (JP)

( * ) Notice: Subject to any disclaimer, the term of this patent is extended or adjusted under 35 U.S.C. 154(b) by 487 days.

(21) Appl. No.: 15/756,803

(22) PCT Filed: Sep. 1, 2016

(86) PCT No.: PCT/JP2016/075733
§ 371 (c)(1),
(2) Date: Mar. 1, 2018

(87) PCT Pub. No.: WO2017/038956
PCT Pub. Date: Mar. 9, 2017

(65) Prior Publication Data
US 2018/0246077 A1 Aug. 30, 2018

(30) Foreign Application Priority Data
Sep. 2, 2015 (JP) .............................. JP2015-172879

(51) Int. Cl.
*G01N 27/416* (2006.01)
*G01N 27/30* (2006.01)
(Continued)

(52) U.S. Cl.
CPC ............... *G01N 33/49* (2013.01); *C12M 1/34* (2013.01); *C12Q 1/26* (2013.01); *C12Q 1/37* (2013.01);
(Continued)

(58) Field of Classification Search
CPC . C12Q 1/26; C12Q 1/27; C12Q 1/005; C12Q 1/001; C12Q 1/004; C12Q 1/37;
(Continued)

(56) References Cited

U.S. PATENT DOCUMENTS 6,127,138 A  10/2000 Ishimaru et al.
8,206,563 B2 *  6/2012 Heller ...................... C12Q 1/26
                                                        204/403.01

(Continued)

FOREIGN PATENT DOCUMENTS

CN          1890379 A  *  1/2007  ........... G01N 33/723
JP     2005-512027 A      4/2005
(Continued)

OTHER PUBLICATIONS

International Search Report issued in corresponding International Patent Application No. PCT/JP2016/075733 dated Dec. 6, 2016.
(Continued)

*Primary Examiner* — Gurpreet Kaur
(74) *Attorney, Agent, or Firm* — Morgan, Lewis & Bockius LLP (57) ABSTRACT

A method for measuring a glycated protein in a sample, the method comprising (1) a step of allowing a sample in which a degradation product has been generated from a glycated protein by a protease to react with an oxidoreductase in the presence of an electron mediator to generate a reduced electron mediator; and (2) a step of detecting the reaction state in the step (1) by an electrochemical technique using an interdigitated electrode.

15 Claims, 7 Drawing Sheets (51) Int. Cl.
| | |
|---|---|
| *G01N 33/49* | (2006.01) |
| *C12Q 1/37* | (2006.01) |
| *C12Q 1/26* | (2006.01) |
| *C12M 1/34* | (2006.01) |

(52) U.S. Cl.
CPC ............ *C12Y 105/03* (2013.01); *G01N 27/30* (2013.01); *G01N 27/416* (2013.01); *G01N 2440/38* (2013.01); *G01N 2800/042* (2013.01)

(58) Field of Classification Search
CPC ...... C12N 9/62; G01N 2333/38; G01N 33/68; G01N 33/723; G01N 33/6806; G01N 33/6803; G01N 27/3272; G01N 27/3273; G01N 27/416; G01N 27/30
See application file for complete search history.

(56) References Cited

U.S. PATENT DOCUMENTS

| | | | | |
|---|---|---|---|---|
| 8,993,255 | B2* | 3/2015 | Hirao | G01N 33/723 435/25 |
| 2002/0090632 | A1 | 7/2002 | Buck, Jr. et al. | |
| 2003/0155237 | A1* | 8/2003 | Surridge | G01N 27/3273 204/403.14 |
| 2004/0140209 | A1* | 7/2004 | Choi | G01N 27/3272 204/403.01 |
| 2007/0131565 | A1* | 6/2007 | Fujiwara | G01N 33/66 205/777.5 |
| 2012/0208226 | A1* | 8/2012 | Ikebukuro | C12Q 1/005 435/25 |
| 2015/0362501 | A1 | 12/2015 | Kurita et al. | |

FOREIGN PATENT DOCUMENTS

| | | |
|---|---|---|
| JP | 2007-163440 A | 6/2007 |
| JP | 2009-171874 A | 8/2009 |
| JP | 2013-500729 A | 1/2013 |
| WO | 98/048043 A1 | 10/1998 |
| WO | 2014/112569 A | 7/2014 |

OTHER PUBLICATIONS

Hatada et al., "Development of enzyme sensor for glycated albumin measurement using screen-printed electrode," Abstracts of the 82nd Annual Meeting of the Electrochemical Society of Japan (2015)(see partial English translation).

Hatada et al., "Development of high sensitive enzyme sensor for glycated albumin measurement using disposable interdigitated array electrode," Abstracts of the 83rd Annual Meeting of the Electrochemical Society of Japan, PS94 (2016) (see partial English translation).

Hatada et al., "Development of a screen-printed carbon electrode based disposable enzyme sensor strip for the measurement of gycated albumin," Biosensors and Bioelectronics, 88: 167-173 (2016).

Hatada et al., "Disposable interdigitated array electrode employing high sensitive enzyme sensor for glycated albumin measurement," 26th Anniversary World Congress on Biosensors, Abstract 1078 (2015).

International Preliminary Report on Patentability and Written Opinion issued in corresponding International Patent Application No. PCT/JP2016/075733 dated Mar. 15, 2018.

Ferri et al., "Tuning Fructosyl Peptidyl Oxidase into Dehydrogenase and Its Application for the Construction of an Enzyme Electrode," ECS Transactions, 35: 113-116 (2011).

Chawla et al., "An amperometric hemoglobin A1c biosensor based on immobilization of fructosyl amino acid oxidase onto zinc oxide nanoparticles-polypyrrole film," Analytical Biochemistry, 430: 156-162 (2012).

Kim et al., "Construction of engineered fructosyl peptidyl oxidase for enzyme sensor applications under normal atomspheric conditions," Biotechnology Letters, 34:491-497 (2012).

Partial Supplemental European Search Report issued in corresponding European Patent Application No. 16841985.1 dated Feb. 8, 2019.

Huang et al., "A Redox-Enzyme-Based Electrochemical Biosensor with a CMOS Integrated Bipotentiostat," Biomedical Circuits and Systems Conference, IEEE, XP031595018, 29-32 (2009).

* cited by examiner

METHOD FOR MEASURING GLYCATED PROTEIN USING INTERDIGITATED ELECTRODE

TECHNICAL FIELD

The present invention relates to a method for measuring a glycated protein in a sample and a biosensor for the measurement.

BACKGROUND ART

It is known that the blood level of glycated proteins reflects the average blood glucose level over a certain period in the past and the measured value of the blood level can be an important indicator for diagnosis and management of symptoms of diabetes mellitus. As the glycated proteins, hemoglobin A1c (HbA1c), which is the glycated protein of hemoglobin, and glycated albumin (GA), which is the glycated protein of albumin, are known. The blood level of glycated proteins is a stable indicator reflecting the blood glucose level over a long period (several weeks to several months) and is therefore useful for judging whether or not the glycemic control that is performed for diagnosing or treating diabetes mellitus is successful.

As a method for measuring the blood level of a glycated protein, Patent Literature 1 discloses a method using a fructosyl amino acid oxidase (hereinafter, may be referred to as "FAOD"). In the method disclosed in Patent Literature 1, a sample is pretreated with a protease to degrade a glycated protein into glycated peptides and glycated amino acids before the reaction between the sample and FAOD, and thereby the reaction rate of FAOD is enhanced, and the detection sensitivity for the glycated protein is enhanced. The titer of FAOD can be measured by using a known method, such as a colorimetric method, a fluorescent method, and an electrochemical method.

Furthermore, various procedures, in which about 0.3 to 10 microliters (μL) of a liquid sample is sucked into a sensor unit, the sample is treated with a variety of reagents in the sensor unit, and the reaction is measured to analyze the sample, have been proposed. In particular, a biosensor that can measure the concentration of a specific substance in a sample by utilizing the substrate specificity of an enzyme used as a reagent is suitable for analysis of a biological sample containing a variety of substances and therefore has been used not only as medical test equipment but also in various fields. Patent Literature 2 discloses a known example of application of such a biosensor to measurement of the blood level of a glycated protein. In the biosensor disclosed in Patent Literature 2, FAOD is immobilized on an electrode together with an artificial electron mediator by a water-soluble photocurable resin, and the glycated protein concentration is measured by an electrochemical method.

Furthermore, Patent Literature 3 discloses a method for measuring a blood component, such as glucose, by applying a biosensor including an interdigitated electrode to the measurement. In the method disclosed in Patent Literature 3, the biosensor having an interdigitated electrode oxidizes the blood component by an oxidoreductase and detects the oxidation current due to the reaction product with the electrode to measure the blood component.

CITATION LIST

Patent Literature

Patent Literature 1: International Publication No. WO 98/48043

Patent Literature 2: Japanese Patent Laid-Open No. 2009-171874

Patent Literature 3: International Publication No. WO 2014/112569

SUMMARY OF INVENTION

Technical Problem

The methods for measuring glycated proteins disclosed in Patent Literatures 1 and 2 use known methods, such as electrical measuring methods, in measurement of the titer of FAOD and both show insufficient sensitivity and data stability, leading to difficulty in practical application. The measurement method using a biosensor disclosed in Patent Literature 3 relates to measurement of a blood component, such as glucose, and application of the method to measurement of a glycated protein is unknown.

It is an object of the present invention to solve these problems and to provide a highly sensitive method for measuring the concentration of a glycated protein in a sample easily and inexpensively.

Solution to Problem

The present inventors have diligently studied to solve the above-described problems and has found that the concentration of a glycated protein in a sample can be highly sensitively quantified easily and inexpensively, surprisingly, by allowing a combination of an electron mediator and an interdigitated electrode to react with a sample that has been brought into contact with a protease for generating a degradation product from the glycated protein, and the present invention has been accomplished.

That is, the present invention relates to the following aspects.

[1] A method for measuring a glycated protein in a sample, comprising (1) a step of allowing a sample in which a degradation product has been generated from a glycated protein by a protease to react with an oxidoreductase in the presence of an electron mediator to generate a reduced electron mediator; and (2) a step of detecting the reaction state in the step (1) by an electrochemical technique using an interdigitated electrode.

[2] The measuring method according to aspect [1], wherein a composition comprising the oxidoreductase and the electron mediator is disposed on the interdigitated electrode.

[3] The measuring method according to aspect [1] or [2], wherein the oxidoreductase is a fructosyl amino acid oxidase.

[4] The measuring method according to any one of aspects [1] to [3], wherein the electron mediator is hexaammineruthenium(III) chloride.

[5] The measuring method according to any one of aspects [1] to [4], wherein the electrochemical technique is a constant potential amperometry.

[6] The measuring method according to any one of aspects [1] to [5], wherein the glycated protein is glycated albumin.

[7] The measuring method according to any one of aspects [1] to [6], wherein the interdigitated electrode has a total area of 1.8 mm$^2$ to 4 mm$^2$, an interelectrode distance of less than 50 μm, a working electrode width of 5 μm to 50 μm, and a counter electrode width of 5 μm to 100 μm.

[8] The measuring method according to aspect [3], wherein a concentration of the fructosyl amino acid oxidase in the step (1) is 12 U/mL or more.

[9] The measuring method according to aspect [4], wherein a concentration of the hexaammineruthenium(III) chloride in the step (1) is 300 mmol/L or more.

[10] A biosensor for measuring a glycated protein in a sample, comprising (1) a composition comprising an electron mediator and an oxidoreductase and (2) an interdigitated electrode, wherein a degradation product generated from a glycated protein by a protease is allowed to react with the oxidoreductase.

[11] A biosensor for measuring glycated albumin in a sample, comprising (1) a composition comprising 300 mmol/L or more of hexaammineruthenium(III) chloride and 12 U/mL or more of a fructosyl amino acid oxidase and (2) an interdigitated electrode having a total area of 1.8 mm$^2$ to 4 mm$^2$, an interelectrode distance of less than 50 µm, a working electrode width of 5 µm to 50 µm, and a counter electrode width of 5 µm to 100 µm, wherein the composition comprising the fructosyl amino acid oxidase and the hexaammineruthenium(III) chloride is disposed on the interdigitated electrode; and a degradation product generated from the glycated protein being in contact with a protease is allowed to react with the fructosyl amino acid oxidase.

Advantageous Effects of Invention

According to the present invention, the concentration of a glycated protein in a sample can be highly sensitively quantified easily and inexpensively by allowing a combination of an electron mediator and an interdigitated electrode to react with a sample in which a degradation product has been generated from the glycated protein by a protease.

DESCRIPTION OF EMBODIMENTS

Embodiments of the present invention (hereinafter, referred to as "the embodiment") will now be specifically described. However, it should not be understood that the following embodiments are intended to limit the present invention.

The embodiment relates to a method for measuring a glycated protein in a sample, the measuring method comprising:

(1) a step of allowing a sample in which a degradation product has been generated from a glycated protein by a protease to react with an oxidoreductase in the presence of an electron mediator to generate a reduced electron mediator; and (2) a step of detecting the reaction state in the step (1) by an electrochemical technique using an interdigitated electrode.

The glycated protein to be measured by the method according to the embodiment may be any glycated product of a protein without particular limitation. For example, a substance obtained by forming a Schiff's base by a Maillard reaction between an amino group in a protein and a saccharide and subjecting the Schiff's base to Amadori rearrangement is preferred, but the glycated protein is not limited thereto. Specifically, an example of the glycated protein is glycated albumin.

The "sample in which a degradation product has been generated from a glycated protein by a protease" refers to a sample that has been subjected to a process of bringing a protease into contact with a glycated protein possibly contained in the sample for generating a degradation product of the glycated protein, but whether or not the degradation product has actually been generated is not a matter. Although the sample is one possibly containing a glycated protein, the result of measurement may reveal that the sample does not contain the glycated protein.

The protease may be any protease that can degrade a glycated protein into a substrate of an oxidoreductase without particular limitation, and examples thereof include animal-derived proteases, such as trypsin and chymotrypsin; plant-derived proteases, such as papain and bromelain; and microorganism-derived proteases.

Examples of the microorganism-derived protease include *Bacillus*-derived proteases, represented by orientase 22BF (manufactured by HBI Enzymes Inc.), etc.; *Aspergillus*-derived proteases, represented by protease type-XIII (manufactured by Sigma-Aldrich), etc.; *Penicillium*-derived proteases, represented by PD enzyme (manufactured by Kikkoman Corporation), etc.; *Streptomyces*-derived proteases, represented by Pronase; Lysobacter-derived proteases, such as Endoproteinase Lys-c (manufactured by Sigma-Aldrich); Yeast-derived proteases, represented by Proteinase A (manufactured by Sigma-Aldrich), etc.; Tritirachium-derived proteases, represented by Proteinase K (manufactured by Sigma-Aldrich), etc.; *Thermus*-derived proteases, represented by Aminopeptidase T (manufactured by Boehringer Mannheim), etc.; Pseudomonus-derived proteases, represented by Endoproteinase Asp-N (manufactured by Wako Pure Chemical Industries, Ltd.), etc.; and *Achromobacter*-derived proteases, represented by Lysyl endopeptidase (manufactured by Wako Pure Chemical Industries, Ltd.), etc. These specific proteases are mere examples, and the microorganism-derived protease is not limited thereto. A preferred example is orientase 22BF (manufactured by HBI Enzymes Inc.).

The electron mediator according to the embodiment is not particularly limited. For example, potassium ferricyanide, m-PMS (1-methoxy-5-methylphenazinium methyl sulfate), and hexaammineruthenium(III) chloride can be used. Preferably, the electron mediator is hexaammineruthenium(III) chloride.

The concentration of the electron mediator in the step (1) is not particularly limited as long as a glycated protein can be measured. In the case of hexaammineruthenium(III) chloride, the concentration is, for example, 300 mmol/L or more. If the concentration is lower than 300 mmol/L, a current necessary for measurement may not be obtained in some cases.

The oxidoreductase according to the embodiment is not particularly limited and is, for example, a fructosyl amino acid oxidase (FAOD) of which the substrate is a protease degradation product of a glycated protein for the concentration measurement. Specifically, fructosyl amino acid oxidases derived from the genus *Gibberella*, the genus *Aspergillus*, the genus *Candida*, the genus *Penicillium*, the genus *Fusarium*, the genus *Acremonium*, or the genus *Debaryomyces* can be used, but the FAOD is not limited thereto. The concentration of the FAOD in the step (1) is not particularly limited as long as a glycated protein can be measured, and is, for example, 12 U/mL or more, preferably 60 U/mL or more. If the concentration is less than 12 U/mL, a current necessary for measurement may not be obtained in some cases.

The interdigitated electrode in the method according to the embodiment includes working and counter electrodes that are alternately arranged. The shape of the interdigitated electrode is not particularly limited as long as a glycated protein can be measured and the interdigitated electrode has, for example, a total area of 1.8 $mm^2$ to 4 $mm^2$, an interelectrode distance of less than 50 µm, a working electrode width of 5 µm to 50 µm, and a counter electrode width of 5 µm to 100 µm.

Examples of the method for producing the interdigitated electrode according to the embodiment include the following four methods.

(1) A noble metal film is formed on an electrically insulating base material. A resist is printed in a comb shape on the film by screen printing, and the noble metal film in the portion not covered with the resist is etched. The resist is then removed to form an interdigitated electrode.

(2) A noble metal film is formed on an electrically insulating base material. A resist is applied or pasted on the film and is exposed to light through a photomask to cure the resist in the portion forming an interdigitated electrode. The resist and the noble metal film other than the portion forming an interdigitated electrode are then etched, and the resist in the portion forming an interdigitated electrode is removed to form an interdigitated electrode.

(3) A template cut into an interdigitated electrode pattern to be produced is overlaid on an electrically insulating base material. A noble metal film is formed on the electrically insulating base material through the template, and the template is then removed to form an interdigitated electrode.

(4) A resist is printed by screen printing on an electrically insulating base material in the portion not forming an interdigitated electrode, and a noble metal film is formed on the electrically insulating base material and the resist. The resist and the noble metal film formed on the resist are then removed to form an interdigitated electrode.

Examples of the material for the electrically insulating base material include polyester resin, polyethylene terephthalate, and engineering plastic. Examples of the noble metal include gold, platinum, silver, palladium, ruthenium, iridium, rhodium, and mixtures thereof. However, the method for producing an interdigitated electrode is not limited to those described above.

The electrochemical technique to be used in the method according to the embodiment may be a known method, such as a constant potential method, but is not limited thereto.

An example of the principle of measuring a glycated protein by a constant potential method is as follows. First, a protease is brought into contact with a glycated protein in a sample for generating a degradation product of the glycated protein. Subsequently, the generated degradation product of the glycated protein is oxidized by an oxidoreductase. The oxidation reaction of the degradation product reduces the electron mediator as an electron receptor of the oxidation reaction. Application of a constant potential to the interdigitated electrode reoxidizes the reduced electron mediator and gives a response current. Since the response current intensity correlates with the glycated protein concentration, the concentration of a glycated protein can be measured by measuring the response current value.

In the method of the embodiment, an oxidoreductase is disposed together with an electron mediator on an interdigitated electrode in some cases, but the method is not limited thereto. An electron mediator and an oxidoreductase may be disposed on an interdigitated electrode by a known method. For example, drying for disposition, in which a solution of a mixture of an electron mediator and an oxidoreductase is dropwise applied onto an interdigitated electrode and is then dried, is used, but the method is not limited thereto.

In addition, the embodiment relates to a biosensor for measuring a glycated protein in a sample, the biosensor comprising:

(1) a composition comprising an electron mediator and an oxidoreductase; and (2) an interdigitated electrode, wherein a degradation product generated from a glycated protein by a protease is allowed to react with the oxidoreductase.

The glycated protein to be measured by the biosensor according to the embodiment may be any substance obtained by forming a Schiff's base by a Maillard reaction of an amino group in a protein and a saccharide and subjecting the Schiff's base to Amadori rearrangement, without particular limitation, and the glycated protein is, for example, glycated albumin.

The "sample in which a degradation product has been generated from a glycated protein by a protease" refers to a sample that has been subjected to a process of bringing a protease into contact with a glycated protein possibly contained in the sample for generating a degradation product of the glycated protein, but whether or not the degradation product has actually been generated is not a matter.

The sample is one possibly containing a glycated protein, and the result of measurement may reveal that the sample does not contain the glycated protein. The protease may be any protease that can degrade a glycated protein into a substrate of an oxidoreductase, without particular limitation, and examples thereof include animal-derived proteases, such as trypsin and chymotrypsin; plant-derived proteases, such as papain and bromelain; and microorganism-derived proteases.

Examples of the microorganism-derived protease include *Bacillus*-derived proteases, represented by orientase 22BF (manufactured by HBI Enzymes Inc.), etc.; *Aspergillus*-derived proteases, represented by protease type-XIII (manufactured by Sigma-Aldrich), etc.; *Penicillium*-derived proteases, represented by PD enzyme (manufactured by Kikkoman Corporation), etc.; *Streptomyces*-derived proteases, represented by Pronase, etc.; *Lysobacter*-derived proteases, represented by Endoproteinase Lys-c (manufactured by Sigma-Aldrich), etc.; Yeast-derived proteases, represented by Proteinase A (manufactured by Sigma-Aldrich), etc.; Tritirachium-derived proteases, represented by Proteinase K (manufactured by Sigma-Aldrich), etc.; *Thermus*-derived proteases, represented by Aminopeptidase T (manufactured by Boehringer Mannheim), etc.; Pseudomonus-derived proteases, represented by Endoproteinase Asp-N (manufactured by Wako Pure Chemical Industries, Ltd.), etc.; and *Achromobacter*-derived proteases, represented by Lysyl endopeptidase (manufactured by Wako Pure Chemical Industries, Ltd.), etc. These specific proteases are mere examples, and the microorganism-derived protease is not limited thereto. A preferred example is orientase 22BF (manufactured by HBI Enzymes Inc.).

The electron mediator in the biosensor according to the embodiment is not particularly limited. For example, potassium ferricyanide, m-PMS (1-methoxy-5-methylphenazinium methyl sulfate), and hexaammineruthenium (III) chloride can be used. Preferably, the electron mediator is hexaammineruthenium(III) chloride.

The concentration of the electron mediator is not particularly limited as long as a glycated protein can be measured. In the case of hexaammineruthenium(III) chloride, the concentration is set such that the concentration when a sample solution is added to the biosensor is, for example, 300 mmol/L or more. If the concentration is lower than 300 mmol/L, a current necessary for measurement may not be obtained in some cases.

The oxidoreductase in the biosensor according to the embodiment is not particularly limited and is, for example, a fructosyl amino acid oxidase (FAOD) of which the substrate is a protease degradation product of a glycated protein for the concentration measurement. Specifically, fructosyl amino acid oxidases derived from the genus *Gibberella*, the genus *Aspergillus*, the genus *Candida*, the genus *Penicillium*, the genus *Fusarium*, the genus *Acremonium*, and the genus *Debaryomyces* can be used, but the FAOD is not limited thereto. The concentration of the FAOD is not particularly limited as long as a glycated protein can be measured, and is set such that the concentration when a sample solution is added to the biosensor is, for example, 12 U/mL or more. If the concentration is less than 12 U/mL, a current necessary for measurement may not be obtained in some cases.

The interdigitated electrode in the biosensor according to the embodiment includes alternately arranged working and counter electrodes. The shape of the interdigitated electrode is not particularly limited as long as a glycated protein can be measured, and the interdigitated electrode has, for example, a total area of 1.8 $mm^2$ to 4 $mm^2$, an interelectrode distance of less than 50 µm, a working electrode width of 5 µm to 50 µm, and a counter electrode width of 5 µm to 100 µm.

Examples of the method for producing the interdigitated electrode of the biosensor according to the embodiment include the following four methods:

(1) A noble metal film is formed on an electrically insulating base material. A resist is printed in a comb shape on the film by screen printing, and the noble metal film in the portion not covered with the resist is etched. The resist is then removed to form an interdigitated electrode.

(2) A noble metal film is formed on an electrically insulating base material. A resist is applied or pasted on the film and is exposed to light through a photomask to cure the resist in the portion forming an interdigitated electrode. The resist and the noble metal film other than the portion forming an interdigitated electrode are then etched, and the resist in the portion forming an interdigitated electrode is removed to form an interdigitated electrode.

(3) A template cut into an interdigitated electrode pattern to be produced is overlaid on an electrically insulating base material. A noble metal film is formed on the electrically insulating base material through the template, and the template is then removed to form an interdigitated electrode.

(4) A resist is printed by screen printing on an electrically insulating base material in the portion not forming an interdigitated electrode, and a noble metal film is formed on the electrically insulating base material and the resist. The resist and the noble metal film formed on the resist are then removed to form an interdigitated electrode.

Examples of the material for the electrically insulating base material include polyester resin, polyethylene terephthalate, and engineering plastic. Examples of the noble metal include gold, platinum, silver, palladium, ruthenium, iridium, rhodium, and mixtures thereof. However, the method for producing an interdigitated electrode is not limited to those described above.

The biosensor according to the embodiment detects the reaction state between a degradation product of a glycated protein and an oxidoreductase by an electrochemical technique. The electrochemical technique to be used may be a known method, such as a constant potential method, but is not limited thereto.

An example of the principle of measuring a glycated protein by a constant potential method is as follows. First, a protease is brought into contact with a glycated protein in a sample for generating a degradation product of the glycated protein. Subsequently, the generated degradation product of the glycated protein is oxidized by the oxidoreductase of a biosensor. The oxidation reaction of the degradation product reduces the electron mediator as an electron receptor of the oxidation reaction. Application of a constant potential to the interdigitated electrode reoxidizes the reduced electron mediator and gives a response current. Since the response current intensity correlates with the glycated protein concentration, the concentration of a glycated protein can be measured by measuring the response current value.

In the biosensor according to the embodiment, an oxidoreductase is disposed together with an electron mediator on an interdigitated electrode in some cases, but the biosensor is not limited thereto. An electron mediator and an oxidoreductase may be disposed on an interdigitated electrode by a known method. For example, drying for disposition, in which a solution of a mixture of an electron mediator and an oxidoreductase is dropwise applied onto an interdigitated electrode and is then dried, is used, but the method is not limited thereto.

The embodiment further relates to a biosensor for measuring glycated albumin in a sample, the biosensor comprising:

(1) a composition comprising hexaammineruthenium(III) chloride in amounts set to give a concentration of 300 mmol/L or more when a sample solution is added thereto and a fructosyl amino acid oxidase in amounts set to give a concentration of 12 U/mL or more when a sample solution is added thereto; and (2) an interdigitated electrode having a total area of 1.8 $mm^2$ to 4 $mm^2$, an interelectrode distance of less than 50 µm, a working electrode width of 5 µm to 50 µm, and a counter electrode width of 5 µm to 100 µm, wherein the composition comprising the fructosyl amino acid oxidase and the hexaammineruthenium(III) chloride is disposed on the interdigitated electrode; and a degradation product generated from the glycated protein by a protease is allowed to react with the fructosyl amino acid oxidase.

EXAMPLES

An Example measuring the concentration of glycated albumin (GA) in a sample by using a fructosyl amino acid oxidase (FAOD) will now be described, but it should be noted that the sample to be subjected to measurement or the enzyme is not limited thereto. The measurement of glycated albumin is based on the following principle. GA contained in a sample is digested with a protease to release fructosyl lysine (ε-FK) having a structure in which the amino group on the ε-position of a lysine residue is glycated. The free ε-FK is oxidized by FAOD. The oxidation reaction of ε-FK reduces an artificial electron receptor (mediator) serving as an electron receptor of the oxidation reaction. Application of a constant potential to the interdigitated electrode reoxidizes the reduced mediator and gives a response current. Since the response current intensity correlates with the GA concentration, the concentration of GA can be measured by measuring the response current value. In the following Examples, as a synthetic substrate of ε-FK, benzyloxycarbonyl-fructosyl lysine (Z-FK) in which the amino group on the α-position was masked by a benzyloxycarbonyl group, was used.

(Example 1) Optimization of FAOD Concentration

<Reagent (Final Concentration)>
  10 mmol/L potassium phosphate buffer (PPB) (pH 8.0)
  FAOD (1.2 to 240 U/mL)
  Hexaammineruthenium(III) chloride (100 mmol/L)
<Substrate (Final Concentration)>
  Z-FK solution (0 to 500 μmol/L)
<Used Electrode>
  Interdigitated electrode (the interdigitated electrode, described in International Publication No. WO 2014/112569, developed by Tanaka Kikinzoku Kogyo K.K.)

FAOD was dissolved in 40 mmol/L PPB to give concentrations of 4.8, 9.6, 24, 48, 96, 192, 240, 480, 640, and 960 U/mL. Hexaammineruthenium(III) chloride was dissolved in purified water to give a concentration of 400 mmol/L. Z-FK was dissolved in purified water to give concentrations of 100, 200, 600, and 1000 μmol/L.

Figure 1:
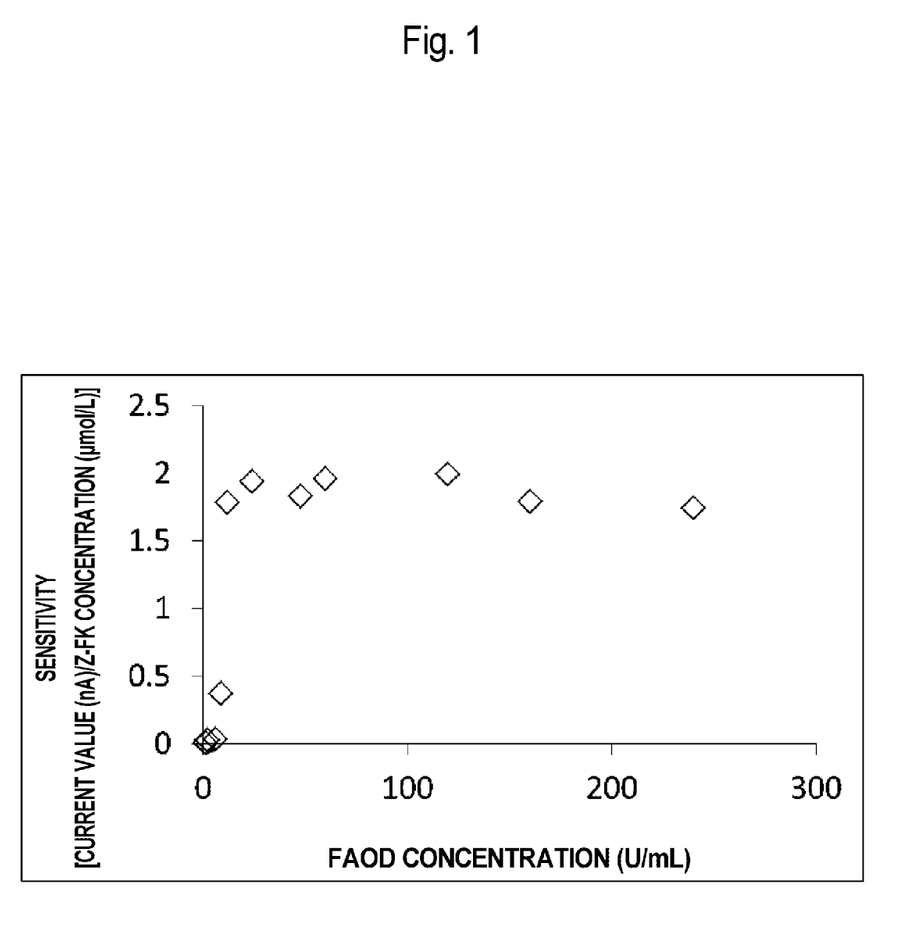
FIG. 1 is a graph showing a relationship between the sensitivity in measurement of benzyloxycarbonyl-fructosyl lysine and the concentration of a fructosyl amino acid oxidase according to an Example.

The FAOD solutions (each 3 μL) were respectively mixed with the hexaammineruthenium(III) chloride aqueous solution (3 μL), and the mixtures were then respectively mixed with 6 μL of the Z-FK aqueous solution or purified water. On this occasion, the final concentration of FAOD was 1.2, 2.4, 6, 9, 12, 24, 48, 60, 120, 160, or 240 U/mL; the final concentration of hexaammineruthenium(III) chloride was 100 mmol/L; and the final concentration of Z-FK was 0, 50, 100, 300, or 500 μmol/L. The mixed solutions (each 3 μL) were respectively dropwise added onto the working and counter electrodes of an interdigitated electrode. After a reaction at room temperature for 60 seconds, constant potential measurement was performed under application of a voltage of 100 mV, and current values after 5 seconds were compared to one another. The results of analysis of the relationship between the sensitivity (current value/Z-FK concentration) and the FAOD concentration showed an FAOD concentration-dependent increase of the sensitivity, as shown in FIG. 1. The results of observation suggested that a final concentration of FAOD of 12 U/mL or more stabilizes the sensitivity and that a final concentration of 60 U/mL or more provides a sufficient reaction efficiency.

(Example 2) Optimization of Mediator Concentration

<Reagent (Final Concentration)>
  10 mmol/L potassium phosphate buffer (PPB) (pH 8.0)
  FAOD (12 U/mL)
  Hexaammineruthenium(III) chloride (1 to 400 mmol/L)
<Substrate (Final Concentration)>
  Z-FK solution (0 to 500 μmol/L)
<Used Electrode>
  Interdigitated electrode (the interdigitated electrode, described in International Publication No. WO 2014/112569, developed by Tanaka Kikinzoku Kogyo K.K.)

FAOD was dissolved in 120 mmol/L PPB to give a concentration of 144 U/mL. Hexaammineruthenium(III) chloride was dissolved in purified water to give concentrations of 4, 40, 200, 400, 600, 800, 1200, and 1600 mmol/L. Z-FK was dissolved in purified water to give concentrations of 75, 150, 450, and 750 μmol/L.

Figure 2:
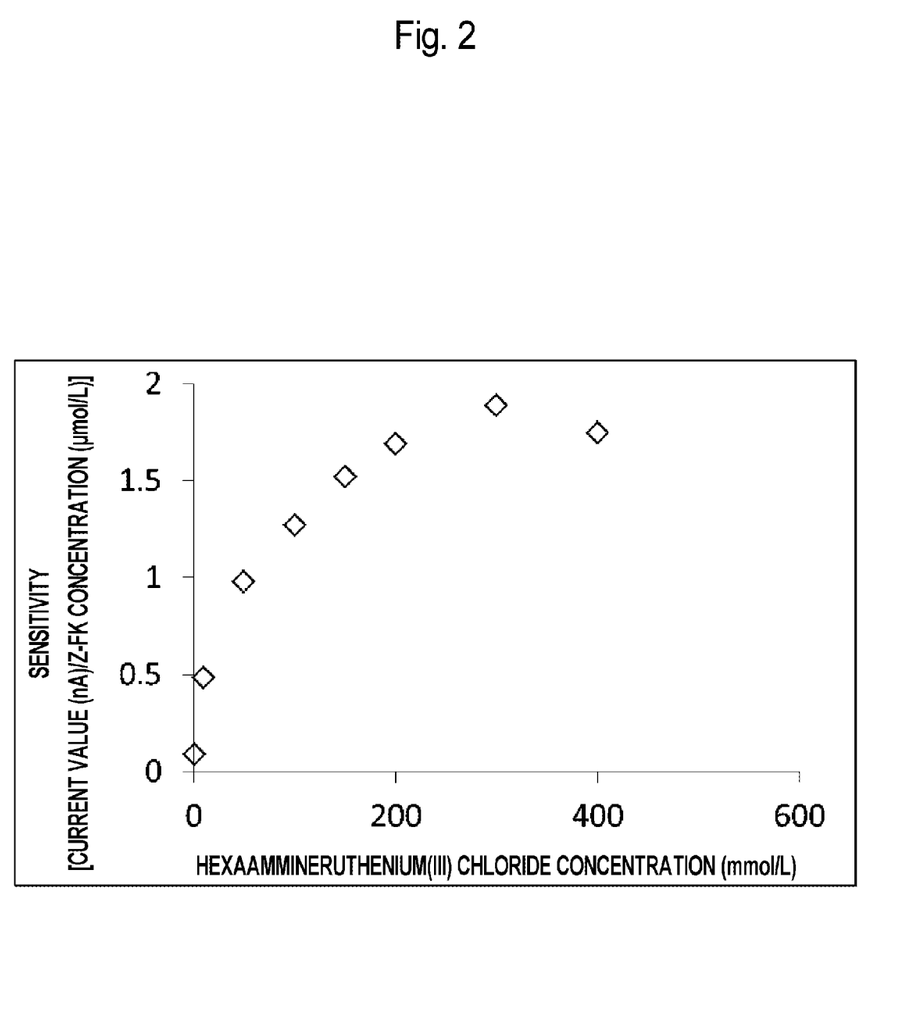
FIG. 2 is a graph showing a relationship between the sensitivity in measurement of benzyloxycarbonyl-fructosyl lysine and the concentration of hexaammineruthenium(III) chloride according to an Example.

The hexaammineruthenium(III) chloride aqueous solutions (each 3 μL) were respectively mixed with the FAOD solution (1 μL), and the mixtures were then respectively mixed with 8 μL of the Z-FK aqueous solution or purified water. On this occasion, the final concentration of FAOD was 12 U/mL; the final concentration of hexaammineruthenium(III) chloride was 1, 10, 50, 100, 150, 300, or 400 mmol/L; and the final concentration of Z-FK was 0, 50, 100, 300, or 500 μmol/L. The mixed solutions (each 3 μL) were respectively dropwise added onto the working and counter electrodes of an interdigitated electrode. After a reaction at room temperature for 60 seconds, constant potential measurement was performed under application of a voltage of 100 mV, and current values after 5 seconds were compared to one another. The results of analysis of the relationship between the sensitivity (current value/Z-FK concentration) and the hexaammineruthenium(III) chloride concentration showed a hexaammineruthenium(III) chloride concentration-dependent increase of the sensitivity, as shown in FIG. 2. The results of observation revealed that a final concentration of hexaammineruthenium(III) chloride of 300 mmol/L or more is preferred.

(Example 3) Comparison of Printed Carbon Electrode and Interdigitated Electrode

<Reagent (Final Concentration)>
  10 mmol/L potassium phosphate buffer (PPB) (pH 8.0)
  FAOD (60 U/mL)
  Hexaammineruthenium(III) chloride (300 mmol/L)
<Substrate (Final Concentration)>
  Z-FK aqueous solution (0 to 500 μmol/L)
<Used Electrode>
  Interdigitated electrode (the interdigitated electrode, described in International Publication No. WO 2014/112569, developed by Tanaka Kikinzoku Kogyo K.K.)
  Printed carbon electrode (manufactured by BioDevice Technology, Ltd.)

FAOD was dissolved in 120 mmol/L PPB to give a concentration of 720 U/mL. Hexaammineruthenium(III) chloride was dissolved in purified water to give a concentration of 1200 mmol/L. Z-FK was dissolved in purified water to give concentrations of 75, 150, 450, and 750 μmol/L.

Figure 3:
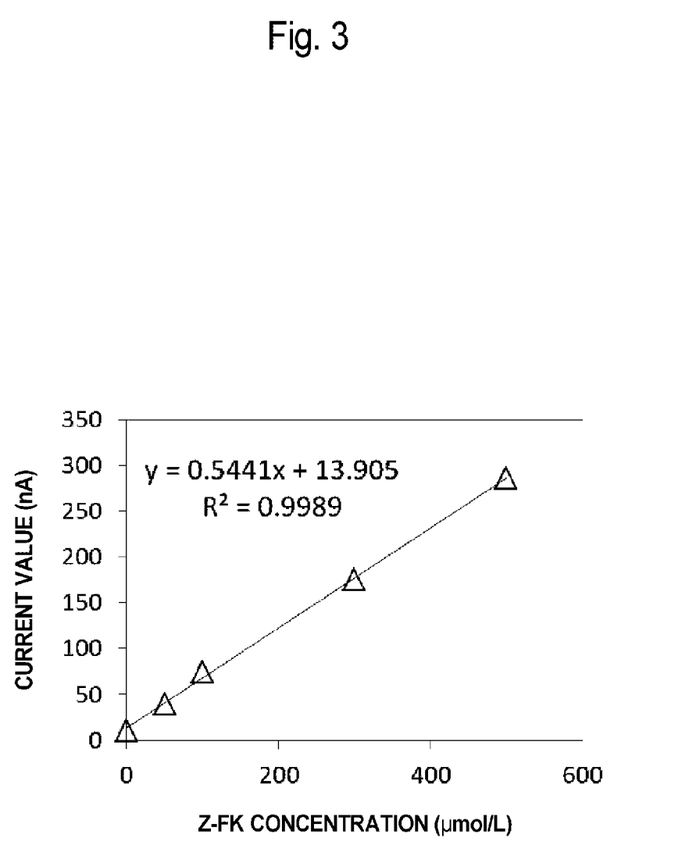
FIG. 3 is a graph showing a standard curve (printed carbon electrode) in benzyloxycarbonyl-fructosyl lysine measurement according to a Comparative Example.
Figure 4:
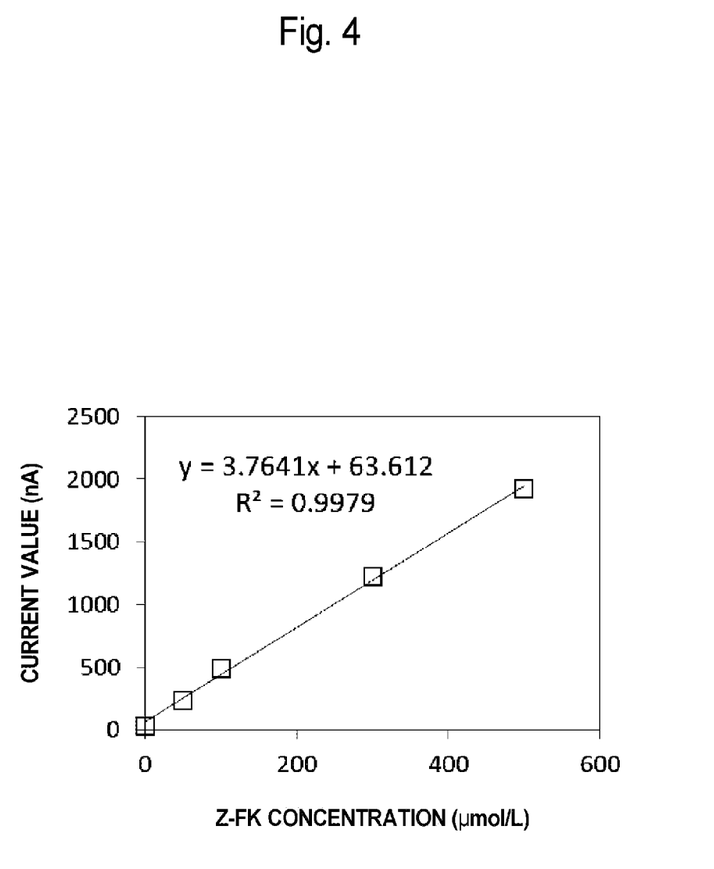
FIG. 4 is a graph showing a standard curve (interdigitated electrode) in benzyloxycarbonyl-fructosyl lysine measurement according to an Example.

The FAOD solution (1 μL) was mixed with the hexaammineruthenium(III) chloride aqueous solution (3 μL). The Z-FK aqueous solutions (each 8 μL) were respectively mixed with the mixture. The mixed solutions (each 3 μL) were respectively dropwise added onto an interdigitated electrode and a printed carbon electrode. After a reaction for 60 seconds, constant potential measurement was performed under application of a voltage of 100 mV, and current values after 5 seconds (interdigitated electrode) and after 20 seconds (printed carbon electrode) were compared to one another. The results of analysis of the correlation between the Z-FK concentration and the current value demonstrated that the slope of the calibration curve in the Z-FK measurement with the interdigitated electrode shown in FIG. 4 was about 7 times compared to the printed carbon electrode shown in FIG. 3. In addition, the current density observed in the use of the interdigitated electrode was higher than that observed in the use of the printed carbon electrode. That is, when the interdigitated electrode and the printed carbon electrode were compared for the value obtained by dividing the observed current value by the area of the working electrode, i.e., the current density, for example, in a Z-FK concentration of 500 μmol/L, which is the highest concentration in this measurement, the current densities were 1.91 $\mu A/mm^2$ and 119 $nA/mm^2$, respectively, and the current density observed in the interdigitated electrode was about 16 times that observed in the printed carbon electrode. Thus, it was revealed that the application of an interdigitated electrode can achieve high sensitivity.

(Example 4) Arrangement of Reagent on Interdigitated Electrode

Figure 5:
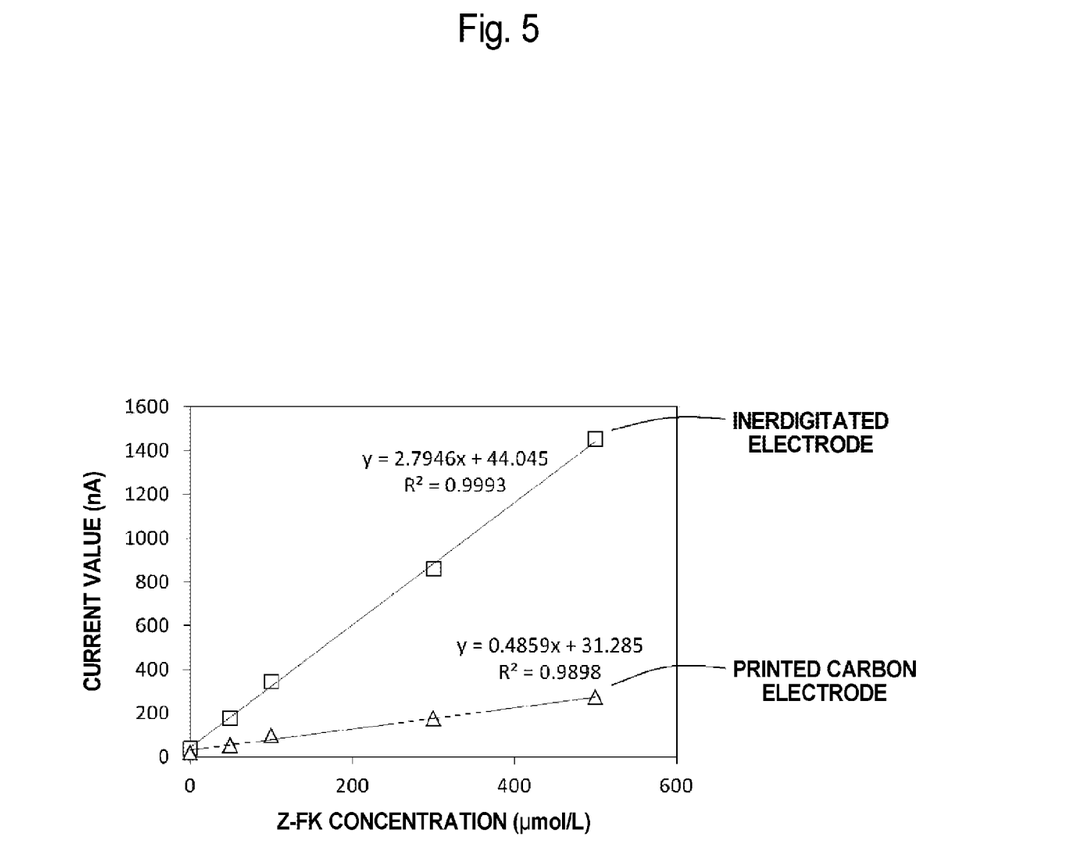
FIG. 5 is a graph showing standard curves in benzyloxycarbonyl-fructosyl lysine measurement using a carbon electrode and an interdigitated electrode on which the reagents according to Example were disposed.

<Reagent (Final Concentration)>
    10 mmol/L potassium phosphate buffer (PPB) (pH 8.0)
    FAOD (60 U/mL)
    Hexaammineruthenium(III) chloride (300 mmol/L)
    Sucrose (0.25%) manufactured by Wako Pure Chemical Industries, Ltd.
<Substrate (Final Concentration)>
    Z-FK aqueous solution (0 to 500 μmol/L)
<Used Electrode>
    Interdigitated electrode (the interdigitated electrode, described in International Publication No. WO 2014/112569, developed by Tanaka Kikinzoku Kogyo K.K.)
    Printed carbon electrode (manufactured by BioDevice Technology, Ltd.)
    FAOD was dissolved in 120 mmol/L PPB to give a concentration of 720 U/mL. Hexaammineruthenium(III) chloride was dissolved in purified water to give a concentration of 1200 mmol/L. Sucrose was dissolved in purified water to give a concentration of 0.375%. Z-FK was dissolved in purified water to give final concentrations of 50, 100, 300, and 500 μmol/L. The FAOD solution (1 μL), the hexaammineruthenium(III) chloride aqueous solution (3 μL), and the sucrose (8 μL) were mixed. An interdigitated electrode and a printed carbon electrode each equipped with a cover were allowed to absorb the mixture in an amount of 0.8 μL and an amount of 1.3 μL, respectively, and were dried in a thermostatic incubator at 25° C. for 30 minutes to produce sensors having FAOD disposed. The produced sensors having FAOD disposed were allowed to absorb the Z-FK solution in an amount of 0.8 μL and in an amount of 1.3 μL, respectively. After a reaction for 60 seconds, constant potential measurement was performed under application of a voltage of 100 mV, and current values after 5 seconds (interdigitated electrode) and after 20 seconds (printed carbon electrode) were compared to one another. The results of analysis of the correlation between the Z-FK concentration and the current value demonstrated, as shown in FIG. 5, that the slope of the calibration curve in the Z-FK measurement using the interdigitated electrode was about 6 times compared to that obtained using the printed carbon electrode. In addition, the current density observed in the use of the interdigitated electrode was higher than that in the use of the printed carbon electrode. That is, when the interdigitated electrode and the printed carbon electrode were compared for the value obtained by dividing the observed current value by the area of the working electrode, i.e., the current density, for example, in a Z-FK concentration of 500 μmol/L, which is the highest concentration in this measurement, the current densities were 1.44 $\mu A/mm^2$ and 114 $nA/mm^2$, respectively, and the current density observed in the interdigitated electrode was about 13 times that observed in the printed carbon electrode. A sensor capable of performing highly sensitive measurement was able to be produced by applying an interdigitated electrode.

(Example 5) Measurement of Protease Digestion Product of Glycated Albumin

Figure 6:
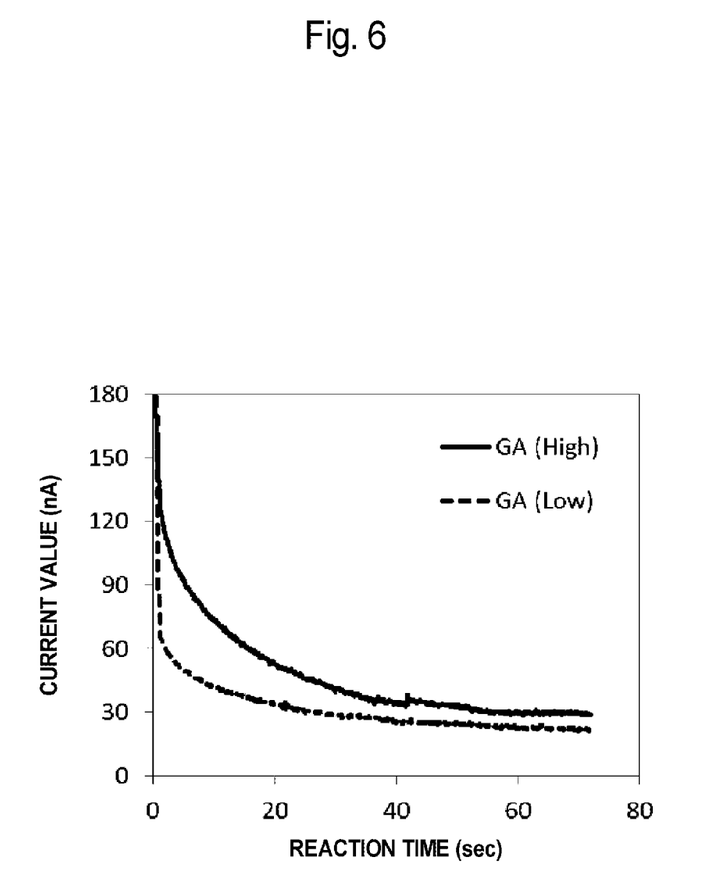
FIG. 6 is a graph showing changes of reaction (printed carbon electrode) over time in measurement of a protease digestion product of glycated albumin according to a Comparative Example.
Figure 7:
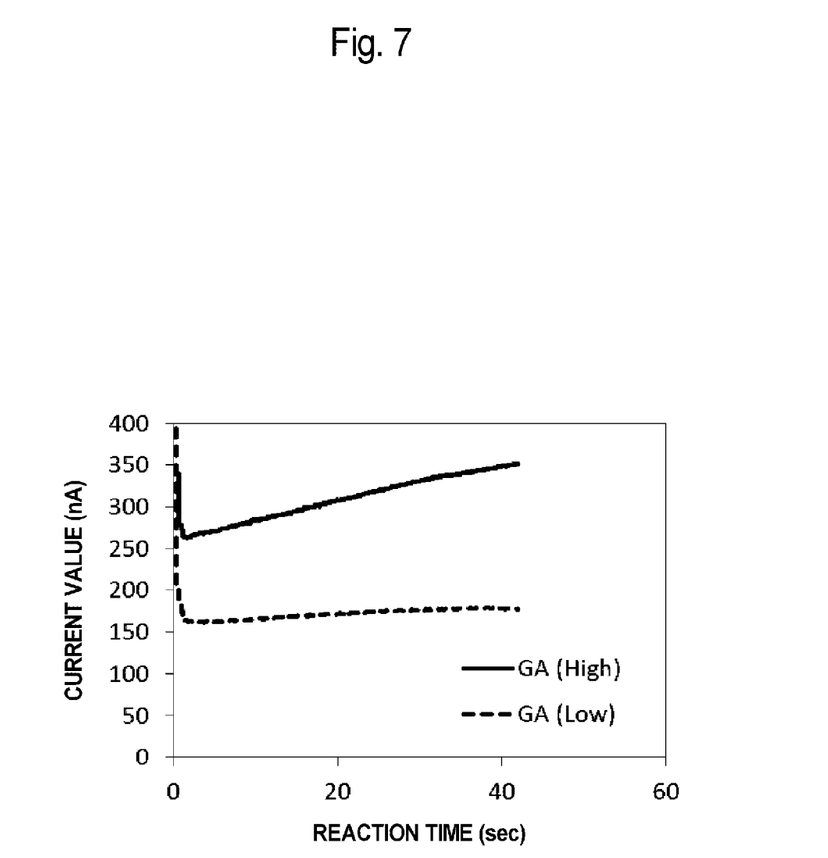
FIG. 7 is a graph showing changes of reaction (interdigitated electrode) over time in measurement of a protease digestion product of glycated albumin according to an Example.

<Sample>
    Glycated albumin (low and high concentrations)
<Reagent 1 (Final Concentration)>
    Orientase 22BF (manufactured by HBI Enzymes Inc.) (50 mg/mL)
<Reagent 2 (Final Concentration)>
    10 mmol/L potassium phosphate buffer (PPB) (pH 8.0)
    FAOD (60 U/mL)
    Hexaammineruthenium(III) chloride (300 mmol/L)
    Sucrose (0.25%) manufactured by Wako Pure Chemical Industries, Ltd.
<Used Electrode>
    Interdigitated electrode (the interdigitated electrode, described in International Publication No. WO 2014/112569, developed by Tanaka Kikinzoku Kogyo K.K.)
    Printed carbon electrode (manufactured by BioDevice Technology, Ltd.)
    Orientase 22BF (manufactured by HBI Enzymes Inc.) was dissolved in purified water to give a concentration of 50 mg/mL. Glycated albumin (low or high concentration) and the orientase 22BF solution were mixed at a volume ratio of 1:1, and were allowed to react with each other at 37° C. for 1 hour to produce a protease digestion product of glycated albumin. Furthermore, FAOD was dissolved in 120 mmol/L PPB to give a concentration of 720 U/mL. Hexaammineruthenium(III) chloride was dissolved in purified water to give a concentration of 1200 mmol/L. Sucrose was dissolved in purified water to give a concentration of 0.375%. Z-FK was dissolved in purified water to give final concentrations of 50, 100, 300, and 500 μmol/L.
    The FAOD solution (1 μL), the hexaammineruthenium(III) chloride aqueous solution (3 μL), and the sucrose (8 μL) were mixed. An interdigitated electrode and a printed carbon electrode each equipped with a cover were allowed to absorb the mixture in an amount of 0.8 μL and an amount of 1.3 μL, respectively, and were dried in a thermostatic incubator at 25° C. for 30 minutes to produce sensors each having FAOD disposed. The sensors having FAOD disposed were allowed to absorb the protease digestion product in an amount of 0.8 μL (interdigitated electrode) and in an amount of 1.3 μL (printed carbon electrode), respectively. After a reaction for 60 seconds, constant potential measurement was performed under application of a voltage of 100 mV, and current values after 5 seconds (interdigitated electrode) and after 20 seconds (printed carbon electrode) were compared to one another. The results of analysis of the difference of the current values in measurement of glycated albumin (low and high concentrations) were that the current value difference in the interdigitated electrode was 104 nA after 5 seconds as shown in FIG. 7, whereas the current value difference in the printed carbon electrode was 21 nA after 20 seconds as shown in FIG. 6. It was demonstrated that high-sensitive measurement is possible by application of an interdigitated electrode also in glycated albumin measurement, compared to a conventional printed carbon electrode.

INDUSTRIAL APPLICABILITY

As described above, according to the method for measuring the concentration of a glycated protein or the biosensor of the present invention, high-sensitive quantification of the concentration of a glycated protein in a sample is possible by easy operation and within a short time. It is accordingly possible to provide a simple and inexpensive analytical instrument that can be used, for example, in a blood test in the clinical diagnostic field, by applying the present invention. Since the blood level of a glycated protein can be an important indicator for diagnosis and management of symptoms of diabetes mellitus, such an analytical instrument can be expected as a useful means for diagnosis and management of symptoms of diabetes mellitus.

The invention claimed is:

1. A method for measuring a glycated albumin protein in a sample, comprising
   (1) a step of allowing the sample in which a degradation product has been generated from a glycated albumin protein by a protease to react with fructosyl amino acid oxidase in the presence of 300 mmol/L or more of hexaammineruthenium (III) chloride to generate a reduced hexaammineruthenium (III) chloride; and
   (2) a step of detecting the reaction state in the step (1) by an electrochemical technique using an interdigitated electrode, wherein the interdigitated electrode has a total area of 1.8 $mm^2$ to 4 $mm^2$, an interelectrode distance of less than 50 µm, a working electrode width of 5 µm to 50 µm, and a counter electrode width of 5 µm to 100 µm,
   wherein a composition comprising the fructosyl amino acid oxidase and the hexaammineruthenium (III) chloride is disposed on the working electrode and the counter electrode, and a concentration of the fructosyl amino acid oxidase in the step (1) is 12 U/mL or more.

2. The method according to claim 1, wherein the electrochemical technique is a constant potential amperometry.

3. The method according to claim 1, wherein a concentration of the fructosyl amino acid oxidase in the step (1) is 60 U/mL or more.

4. The method according to claim 1, wherein the protease comprises animal-derived protease, plant-derived protease or microorganism-derived protease.

5. The method according to claim 4, wherein the microorganism-derived protease comprises *Bacillus*-derived protease, *Aspergillus*-derived protease, *Penicillium*-derived protease, *Streptomyces*-derived protease, Lysobacter-derived protease, Yeast-derived protease, Tritirachium-derived protease, *Thermus*-derived protease, Pseudomonus-derived protease, or *Achromobacter*-derived protease.

6. The method according to claim 4, wherein the animal-derived protease comprises trypsin or chymotrypsin.

7. The method according to claim 4, wherein the plant-derived protease comprises papain or bromelain.

8. The method according to claim 1, wherein the fructosyl amino acid oxidase is derived from the genus *Gibberella*, the genus *Aspergillus*, the genus *Candida*, the genus *Penicillium*, the genus *Fusarium*, the genus *Acremonium*, or the genus Debaryomyces.

9. A biosensor for measuring glycated albumin in a sample, comprising
   (1) a composition comprising 300 mmol/L or more of hexaammineruthenium (Ill) chloride and 12 U/mL or more of a fructosyl amino acid oxidase; and
   (2) an interdigitated electrode having a total area of 1.8 $mm^2$ to 4 $mm^2$, an interelectrode distance of less than 50 µm, a working electrode width of 5 µm to 50 µm, and a counter electrode width of 5 µm to 100 µm, wherein
   the composition comprising the fructosyl amino acid oxidase and the hexaammineruthenium (III) chloride is disposed on the working electrode and the counter electrode; and a degradation product generated from a glycated albumin protein being in contact with a protease is allowed to react with the fructosyl amino acid oxidase.

10. The biosensor according to claim 9, wherein the composition comprises 60 U/mL or more of the fructosyl amino acid oxidase.

11. The biosensor according to claim 9, wherein the protease comprises animal-derived proteases, plant-derived proteases or microorganism-derived proteases.

12. The biosensor according to claim 11, wherein the animal-derived protease comprises trypsin or chymotrypsin.

13. The biosensor according to claim 11, wherein the plant-derived protease comprises papain or bromelain.

14. The biosensor according to claim 11, wherein the microorganism-derived protease comprises *Bacillus*-derived protease, *Aspergillus*-derived protease, *Penicillium*-derived protease, *Streptomyces*-derived protease, Lysobacter-derived protease, Yeast-derived protease, Tritirachium-derived protease, *Thermus*-derived protease, Pseudomonus-derived protease, or *Achromobacter*-derived protease.

15. The biosensor according to claim 9, wherein the fructosyl amino acid oxidase is derived from the genus *Gibberella*, the genus *Aspergillus*, the genus *Candida*, the genus *Penicillium*, the genus *Fusarium*, the genus *Acremonium*, or the genus Debaryomyces.

* * * * *